US00PP11939P2

(12) United States Plant Patent
Cunneen

(10) Patent No.: US PP11,939 P2
(45) Date of Patent: Jun. 19, 2001

(54) ARGYRANTHEMUM PLANT NAMED 'SUMMER STARS PINK'

(75) Inventor: Thomas Michael Cunneen, Balmoral Village (AU)

(73) Assignee: The University of Sydney Plant Breeding Institute, Cobbitty (AU)

( * ) Notice: Subject to any disclaimer, the term of this patent is extended or adjusted under 35 U.S.C. 154(b) by 0 days.

(21) Appl. No.: 09/450,099

(22) Filed: Nov. 29, 1999

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Marguerite Daisy plant named Summer Stars Pink, characterized by its upright and mounding plant habit; dark green fine foliage; freely branching growth habit; freely flowering with numerous inflorescences per plant; inflorescences held above the foliage; and long-lasting double-type inflorescences with pink ray florets and yellow-tipped disc florets that give a yellow "eye" effect to the inflorescence.

1 Drawing Sheet

BACKGROUND OF THE INVENTION

The present invention relates to a new and distinct cultivar of Marguerite Daisy plant, botanically known as *Argyranthemum frutescens* and referred to by the cultivar name 'Summer Stars Pink'.

The new cultivar is a product of a planned breeding program conducted by the Inventor in Cobbitty, New South Wales, Australia. The objective of the breeding program was to develop compact, freely-flowering Marguerite daisies good inflorescence form and floret color.

The new cultivar originated from a cross made by the Inventor in September, 1995, of a proprietary selection of *Argyranthemum frutescens* identified as number X943817.2, as the male or pollen parent, with a proprietary selection of *Argyranthemum frutescens* identified as number X931909.1, as the female or seed parent. The cultivar 'Summer Stars Pink' was discovered and selected by the Inventor as a flowering plant within the progeny of the stated cross in a controlled environment in Glenfield, New South Wales, Australia.

Plants of the new Marguerite Daisy are paler pink in ray floret color, have finer foliage and flower earlier than plants of the male parent, the selection number X943817.2.

Plants of the new Marguerite Daisy are darker pink in ray floret color and differ in inflorescence form compared to plants of the female parent, the selection number X931909.1.

Asexual reproduction of the new cultivar by terminal cuttings in Cobbitty, New South Wales, Australia, has shown that the unique features of this new Marguerite Daisy are stable and are reproduced true to type in successive propagations.

SUMMARY OF THE INVENTION

The new cultivar has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Summer Stars Pink' which distinguish 'Summer Stars Pink' as a new and distinct cultivar:

1. Upright and mounding plant habit.
2. Dark green fine foliage.
3. Freely branching growth habit.
4. Freely flowering with numerous inflorescences per plant; inflorescences held above the foliage.
5. Long-lasting double-type inflorescences with pink ray florets and yellow-tipped disc florets giving a yellow "eye" to the inflorescence.

Plants of the new Marguerite Daisy can be compared to plants of the cultivar 'Summer Melody', disclosed in U.S. Plant Patent Application Ser. No. 09/257,093. In side-by-side comparisons conducted in Encinitas, Calif., plants of the new Marguerite Daisy differ from plants of the cultivar 'Summer Melody' in the following characteristics:

1. Plants of the new cultivar are more vigorous, are taller and have a more open plant habit than plants of the cultivar 'Summer Melody'.
2. Plants of the new cultivar are more freely branching, have longer lateral branches and longer internodes than plants of the cultivar 'Summer Melody'.
3. Plants of the new cultivar have larger and slightly darker green leaves than plants of the cultivar 'Summer Melody'.
4. Plants of the new cultivar have more and larger inflorescences than plants of the cultivar 'Summer Melody'.
5. Inflorescences of plants of the new cultivar have twice as many ray florets than inflorescences of plants of the cultivar 'Summer Melody'.
6. Inflorescences of plants of the new cultivar are crested in the center and appear taller and more mounding than inflorescences of plants of the cultivar 'Summer Melody'.

7. Inflorescences of plants of the new cultivar have yellow centers whereas inflorescences of plants of the cultivar 'Summer Melody' have purple centers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors.

The photograph at the top of the sheet comprises a top perspective view of three typical plants of 'Summer Stars Pink' grown in a 21.5-cm container.

The photograph at the bottom of the sheet comprises close-up views of developing inflorescences and leaves of 'Summer Stars Pink' (top of photograph) and 'Summer Melody' (bottom of the photograph).

DETAILED BOTANICAL DESCRIPTION

The following observations, measurements and values describe three plants of the new cultivar grown in 21.5-cm containers in Encinitas, Calif. For the first six weeks after planting, plants were grown under plastic-covered greenhouses with average day and night temperatures of 23.3 and 18.9° C., respectively, and light levels averaging 3,000 foot-candles. Plants were then grown in full sun with day and night temperatures averaging 18 and 13° C., respectively, and light levels averaging 8,000 foot-candles. Plants were about 17 weeks old after planting a rooted cutting.

Color references are made to The Royal Horticultural Society Colour Chart except where general terms of ordinary dictionary significance are used.

Botanical classification: *Argyranthemum frutescens* cultivar 'Summer Stars Pink'.

Parentage:

*Male or pollen parent.*—Proprietary selection of *Argyranthemum frutescens,* identified as number X943817.2.

*Female or seed parent.*—Proprietary selection of *Argyranthemum frutescens* identified as number X931909.1.

Propagation:

*Type.*—Terminal cuttings.

*Time to initiate roots.*—About 10 days at a temperatures of 20° C.

*Time to develop roots.*—About 21 days at a temperatures of 20° C.

*Root description.*—Numerous, fibrous and freely branching.

Plant description:

*General appearance.*—Inverted triangle; upright and mounding plant habit. Pinnatifid foliage. Erect flower stems that hold the inflorescences above the foliage. Appropriate for various sizes and types of containers.

*Crop time.*—About 17 weeks are required to produce finished flowering plants in 21.5-cm containers from rooted cuttings.

*Plant height.*—About 45 cm from soil level to top of inflorescences.

*Plant width.*—About 42 cm.

*Branching.*—Very freely branching, about 16 lateral branches per plant.

*Vigor.*—Vigorous.

*Lateral branches.*—Length: About 28 cm. Diameter: About 5 mm. Internode length: About 8.5 mm. Texture: Glabrous.

*Stem color.*—Green, 143B to 143C.

*Foliage description.*—Arrangement: Alternate, single. Quantity of leaves per lateral branch: Numerous, about 30 on primary laterals. Shape: Pinnatifid. Apex: Pointed. Base: Attenuate; clasping; sessile. Margin: Five-lobed; deeply incised. Length: About 7.5 cm. Width: About 3.75 cm. Texture: Glabrous and smooth. Durability to stresses: Good, very durable. Leaves have a waxy cuticle that resists water loss. Color: Young leaves, upper surface: Lighter than 147A. Young leaves, lower surface: 147B. Mature leaves, upper surface: 147A. Mature leaves, lower surface: 147B. Venation, upper surface: 147A. Venation, lower surface: 147B.

Flowering description:

*Flowering habit.*—Inflorescences on long peduncles held above the foliage. Double-type composite inflorescence form. Inflorescences are initially flat; as flowers develop, outer ray florets tend to reflex; youngest ray florets incurved giving a mounded crested center to the inflorescence resembling an anemone-type inflorescence. Inflorescences form at upper leaf axils. Florets arranged acropetally on a capitulum. Long-lasting, inflorescences last about two or three weeks. Inflorescences persistent.

*Quantity of inflorescences.*—Freely flowering; typically about 5 to 7 inflorescences and buds per lateral stem; usually about 96 inflorescences and buds per plant.

*Natural flowering season.*—Natural flowering season is spring to early fall. Plants flower continuously during this period.

*Inflorescence size.*—Diameter: About 5 cm. Depth (height): About 1.3 cm. Disc diameter: About 1.5 mm.

*Fragrance.*—None.

*Ray florets.*—Quantity per inflorescence and arrangement: Full inflorescences with numerous ray florets, about 227 ray florets arranged in multiple whorls. Shape: Ligulate. Apex: Very slightly tri-dentate. Base: Acute. Margin: Entire. Length: About 1.9 cm. Width: About 5 mm. Texture: Smooth, satiny. Color: When opening, upper surface: 65B. When opening, lower surface: 65C. Fully opened, upper surface: 75B; fading to 75D with subsequent development. Fully opened, lower surface: 75C.

*Disc florets.*—Shape: Tubular; 4 to 5-lobed. Quantity per inflorescence: Sparse, usually about 5. Disc floret length: About 4 mm. Disc floret width: About 2 mm. Color: Immature and mature, 12A.

*Phyllaries.*—Quantity per inflorescence and arrangement: About 20 per inflorescence; imbricate, three whorls; tightly pressed to the receptacle. Aspect: Cupped. Shape: Elliptic. Apex: Broadly acute. Margin: Entire, outer edges slightly membranous. Length: About 7 mm. Color: Upper surface, 146B to 146C; lower surface, 146A.

*Peduncle.*—Length, first peduncle: About 8 cm. Length, fourth peduncle: About 11 cm. Strength: Moderately strong, inflorescences held above foliage. Angle: Acute. Texture: Smooth. Color: 145A.

*Inflorescence bud.*—Shape: Ovoid. Length: About 1 cm. Diameter: About 6 mm. Color: 62A.

*Reproductive structures.*—Androecium: (Present on disc florets only). Stamens: About five rudimentary stamens in central disc florets only; functionally sterile. Pollen: None observed. Gynoecium: Present on ray and disc florets. Pistil number: One per floret. Pistil length: About 3 mm. Style length: About 1.5 mm. Style color: 10A. Stigma shape: Bilobate. Stigma color: 10A. Ovary color: 145A.

Disease resistance: Resistance to pathogens common to Argyranthemum has not been observed.

Seed production: Seed production has not been observed to date.

It is claimed:

1. A new and distinct Marguerite Daisy plant named 'Summer Stars Pink', as illustrated and described.

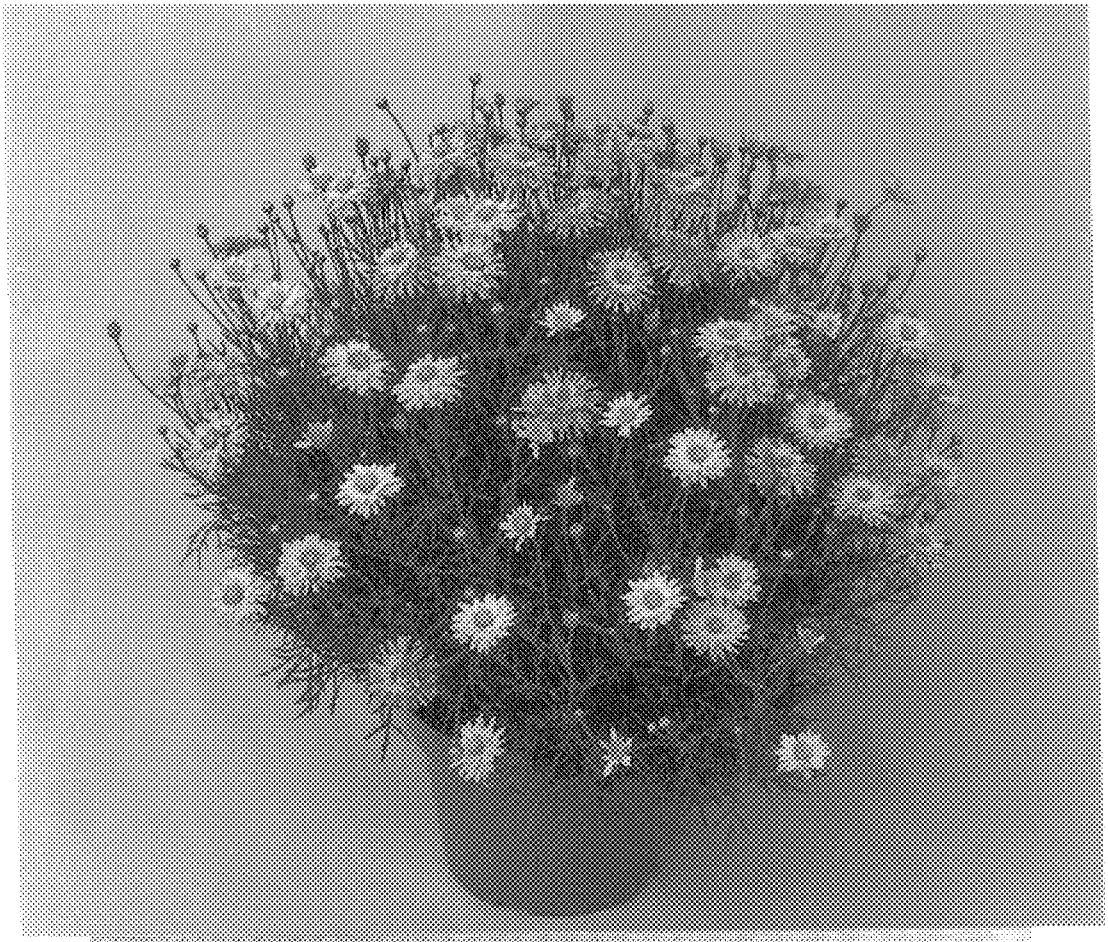
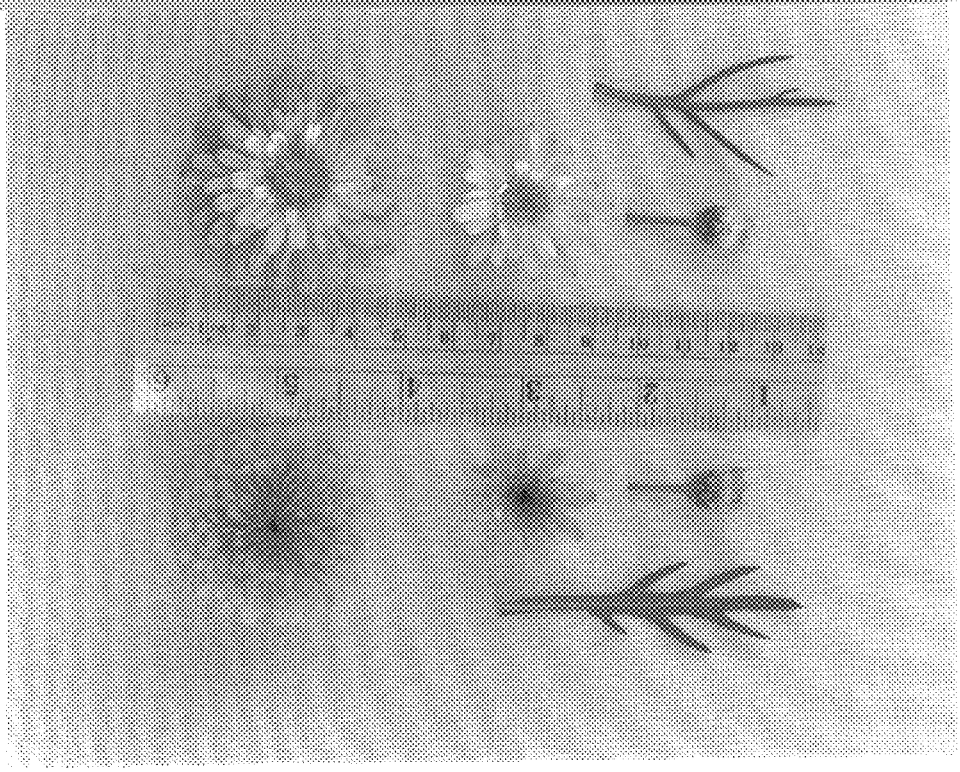

* * * * *